US009757586B2

(12) United States Patent
Dobler et al.

(10) Patent No.: US 9,757,586 B2
(45) Date of Patent: Sep. 12, 2017

(54) MAGNETIC FIELD APPLICATOR FOR THE MAGNETIC STIMULATION OF BODY TISSUES

(71) Applicant: QRS International AG, Ruggell (LI)

(72) Inventors: Karl Dobler, Hohenems (AT); Erwin Fritsch, Hohenems (AT); Gerhard-Emiel Fischer, Kressbronn (DE)

(73) Assignee: QRS INTERNATIONAL AG, Ruggell (LI)

( * ) Notice: Subject to any disclaimer, the term of this patent is extended or adjusted under 35 U.S.C. 154(b) by 353 days.

(21) Appl. No.: 14/475,706

(22) Filed: Sep. 3, 2014

(65) Prior Publication Data

US 2015/0099920 A1    Apr. 9, 2015

(30) Foreign Application Priority Data

Sep. 3, 2013  (DE) ..................... 10 2013 014 913

(51) Int. Cl.
| | | |
|---|---|---|
| *A61N 2/02* | (2006.01) | |
| *H01F 3/00* | (2006.01) | |
| *A61N 2/00* | (2006.01) | |
| *H01F 3/10* | (2006.01) | |
| *H01F 27/245* | (2006.01) | |
| *H01F 27/28* | (2006.01) | |

(52) U.S. Cl.
CPC ............... *A61N 2/02* (2013.01); *A61N 2/004* (2013.01); *H01F 3/10* (2013.01); *H01F 27/245* (2013.01); *H01F 27/2823* (2013.01)

(58) Field of Classification Search
CPC ........ H01F 27/24; H01F 27/2871; H01F 3/10; A61N 2/00–2/02
See application file for complete search history.

(56) References Cited

U.S. PATENT DOCUMENTS

2011/0068783 A1 * 3/2011 Nonogaki ............ G01N 27/902
                                                      324/240

FOREIGN PATENT DOCUMENTS

| DE | 10111678 A1 | 9/2002 | |
|---|---|---|---|
| DE | 102009049145 A1 | 4/2011 | |
| LI | DE 102009049145 | * 4/2011 | ............. A61N 2/006 |

OTHER PUBLICATIONS

Translation of DE102009049145A1, via EPO and Google.*

* cited by examiner

*Primary Examiner* — Charles A Marmor, II
*Assistant Examiner* — Thaddeus Cox
(74) *Attorney, Agent, or Firm* — Browdy and Neimark, PLLC

(57) ABSTRACT

A magnetic field applicator for the magnetic stimulation of body tissues comprising a core carrier (1) in which a plurality of magnetically conductive flow guide pieces comprised of layered iron sheets is disposed, upon which at least one live coil (3) is disposed that generates an upward-emitted magnetic field having a plurality of field line bundles (8), wherein the magnetic field applicator comprises a polygonal coil (3) that is wound as a pancake coil in one or more planes in such a way that the direction of the individual coil conductors (27) is selected such that the coil conductors (27) run in pieces in a predominantly straight line and perpendicular to the plane of the flow guide pieces that are made of layered sector iron cores (5-8).

Figure 1:
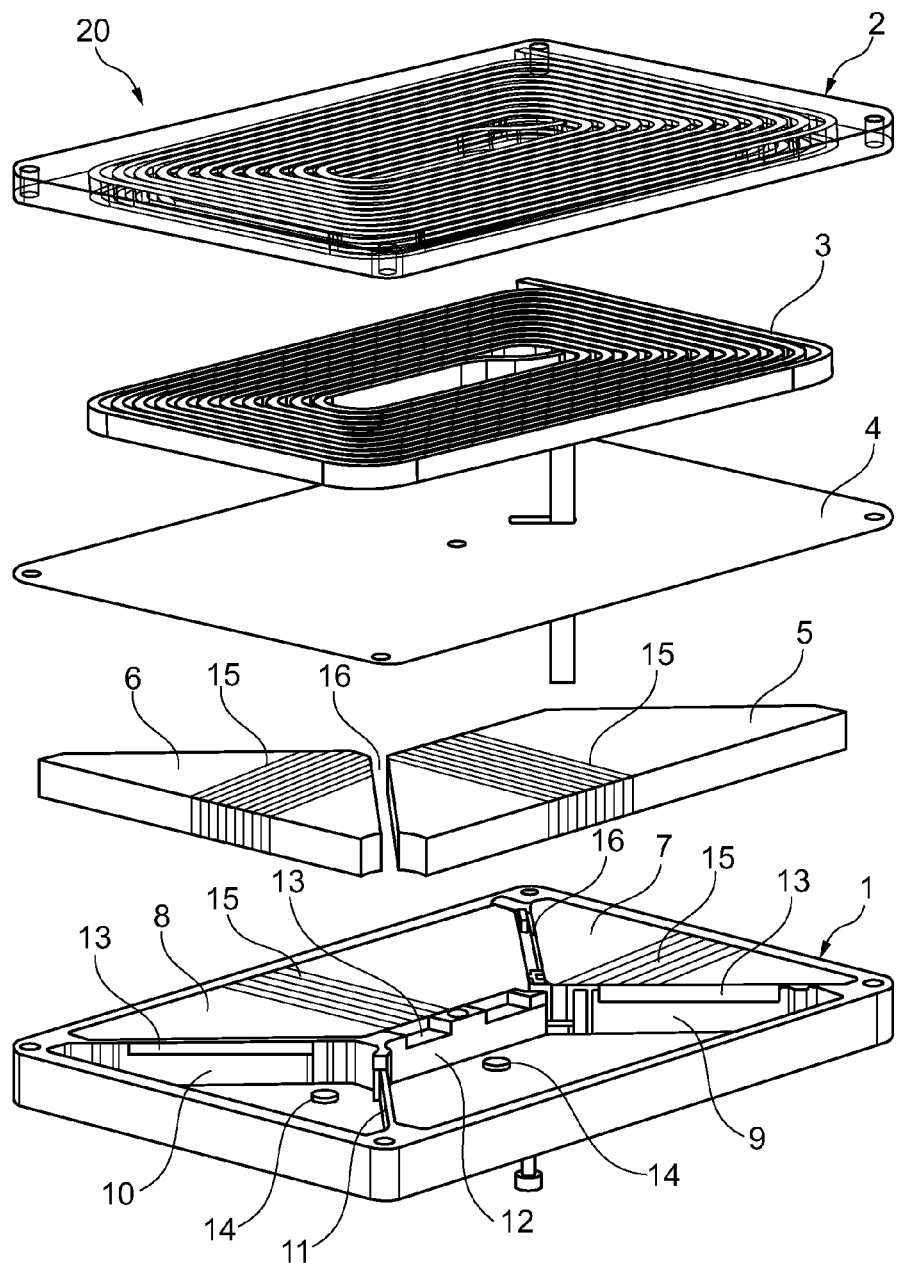

18 Claims, 7 Drawing Sheets ical losses.
MAGNETIC FIELD APPLICATOR FOR THE MAGNETIC STIMULATION OF BODY TISSUES The invention relates to a magnetic field applicator for the magnetic stimulation of body tissues according to the pre-characterizing portion of claim 1.

Such a magnetic field applicator became known, for example, with the subject matter of DE 10 2009 049 145 A1. The specification and purpose detailed therein are hereby incorporated in full by reference into the disclosure of the present invention.

The known magnetic field applicator is a coil carrier in which four terminal shoes are arranged distributed along the circumference, such that this arrangement is also referred to as a quadrupole magnetic field arrangement.

The inside ends of the four terminal shoes, which are designed in a horseshoe shape or C-shape, each encroach into the inner space of the coil while the radially outer ends of the terminal shoes are held in the core carrier. Together, they form an approximately cruciform shape.

The disadvantage of this arrangement is that the terminal shoes do not completely fill the inner space of the core carrier. Rather, open edge regions are left in which the field lines of the magnetic field are no longer guided by an iron core of a terminal shoe. Thus, in these regions, the magnetic field bundle is weakened, which is preferably supposed to be emitted upward parallel to the base surface of the core carrier so as to be introduced in this manner into human body tissue. The purpose of the magnetic field applicator in this document is the same as that of the magnetic field applicator according to the present invention.

Thus, a disadvantage of the known arrangement was the fact that a relatively weak and also somewhat undirected magnetic field was generated, which is in need of improvement.

An additional disadvantage is the fact that the surrounding area of the terminal shoes located toward the outside in the core carrier relative to the coil is filled by terminal shoes only intermittently. In principle, the terminal shoes fill only a small portion of the area on the outer circumference of the coil, while the regions located therebetween are not occupied by the surface of the terminal shoes, which leads to an uneven and weak generation of an upward-directed magnetic field.

An ideal magnetic field distribution for the magnetic stimulation of the urogenital tract in body tissue is predicated on a magnetic field in approximately the shape of a sphere that is intended to fill the entire urogenital tract as evenly as possible with a high intensity. In other words, an upward-directed, spherical, homogenous magnetic field should be produced. This requirement is not fulfilled by the magnetic field generated by the magnetic field applicator according to DE 10 2009 049 145 A1 because, at high current intensity, it generates a great deal of heat caused by eddy current losses.

As a result of the many open spaces that result on the outer circumference of the magnetic coil in the direction of the horseshoe-shaped terminal shoes located outward, the generation of a vertically upward-directed magnetic field is compromised and weakened.

Therefore, based on the subject matter of DE 10 2009 049 145 A1, the object of the invention is to refine a magnetic field applicator for the magnetic stimulation of body tissues, in particular for the stimulation of the urogenital tract, in such a way that the filling of the urogenital tract or other body part to be stimulated with high-intensity magnetic field in as spherical a shape as possible is guaranteed with small electrical losses.

In order to attain the above-mentioned object, the invention is characterized by the technical teaching of claim 1.

An essential feature of the invention is the fact that the magnetic field applicator essentially comprises a polygonal coil that is wound as a pancake coil in such a way that the direction of the individual coil conductors is selected such that pieces of the coil conductors run in a straight line to the greatest extent possible and are respectively oriented perpendicular to the layered sector iron core, with the iron core comprising a plurality of sector iron cores comprised of multiple iron parts evenly distributed on the circumference of the coil carrier, forming an almost closed iron body on whose top and/or bottom side the coil conductors of the coil running in a straight line to the greatest extent possible are disposed.

The present technical feature results in the advantage that different coil shapes may be used such as, for example, a rectangular coil, a polygonal coil, or a triangular coil.

Therefore, it is important in the invention that square, triangular, polygonal, or rectangular pancake or cylindrical coils may be used, having predominantly straight paths of the conductors disposed therein. A unilateral arrangement of sector iron cores below or above the respective winding plane of the pancake coil is present and each sector iron core preferably comprises a plurality of thin, magnetically conductive sheets electrically insulated from one another, of which each sheet is preferably oriented transversely to the longitudinal extension of the coil conductor. The sector iron cores, i.e., the sheet packet, should be assembled as compactly as possible.

This results in the advantage that the coil shape overall is selected such that the coil conductors of the coil run in a straight line to the greatest extent possible. This is understood to mean that they run in a straight line parallel to one another over large areas of their path, i.e., without a radius and, in so doing, are disposed on or below the sheet packet. The arrangement of the sector iron cores with the iron sheets as described is selected such that all of the layered iron cores run with their planes perpendicular to the longitudinal axis of the respective coil conductor. The straighter the lines in which the coil conductors run, the more regions of the coil conductor there are that run in a precisely perpendicular fashion to the plane of the layered iron sheets of the sector iron core.

Thus, for the first time, a pancake coil is formed that is completely filled by sector iron cores, with each sector iron core comprising a plurality of iron sheets adhered to and insulated from one another, forming an iron sheet packet.

The plane through all layered iron sheets of the sector iron cores is thus perpendicular to the longitudinal extension of the coil conductor, insofar as it runs in a straight line. This is the reason why the invention requires that the coil conductor run in a straight line for as long as possible and that only brief stretches of curve deviating therefrom be present in which the advantage of a perpendicular orientation of the (straight) coil conductor running perpendicular to the plane of the iron sheets is not obtained.

It is also preferable for a so-called rectangular conductor to be used as the coil conductor that is essentially comprised of a plurality of round strands insulated from one another and twisted with one another.

It is preferable for these round strands to be arranged twisted relative to one another such that they fill out the contour of such a rectangular conductor in the manner of a twisted braid or a twisted band.

Instead of such a rectangular conductor, however, square conductors may also be used whose interior also comprises a plurality of round strands twisted with one another and insulated from one another.

In order to counteract the effect of current displacement losses, it is therefore preferable for the rectangular or square conductor to be filled by a plurality of round strands insulated from one another and twisted together, with each round strand being located once in the interior of the rectangular or square conductor and once on its outer wall in order to allow an even penetration of the entire inner profile of the rectangular or round conductor.

It is preferred for rectangular conductors to be used that stand upright relative to the plane on which they are placed and therefore also upright relative to the sector iron cores located therebelow or thereabove. Due to the high current flow, a certain minimum cross-section is a precondition for the coil conductor in order to prevent undesired instances of heating.

In order to achieve the greatest possible magnetic field output in the upward direction, it is therefore preferable for rectangular conductors to be used that stand upright and are placed parallel to one another in a plane because this allows the number of windings to be increased while keeping the same conductor cross-section.

However, the invention is not limited to the use of rectangular conductors placed in one plane parallel to one another and in an approximately spiral arrangement. The conductors may also be placed in two or more planes. Instead of such rectangular conductors, round conductors or polygonal conductors may also be used, even though this would result in a lower emission effect for an upward-directed magnetic field or higher losses with the same current intensity. Regardless, such a lower-quality embodiment is also included in the scope of the invention.

In such an arrangement of flat coil conductors, which are preferably embodied as rectangular conductors, in conjunction with sector iron cores comprising layered iron sheets and extending over the entire area of the coil conductor, the advantage results that the desired spherical magnetic field emitted in the upward direction with a high magnetic flow density is achieved with a good approximation of a spherical or Gaussian shape.

On the other hand, only minor losses (heat, impedance, and conduction losses) occur during operation, such that, with a predetermined magnetic field strength, a significantly lower current use with significantly lower cooling requirements results.

The object of the present invention results not only from the subject matter of the individual claims, but also from the combination of the individual claims with one another.

All information and features disclosed in the documents, including the abstract, in particular the spatial design disclosed in the drawings, are hereby claimed as essential to the invention insofar as they are novel as compared to the prior art, either individually or in combination.

The invention shall be described in greater detail below with reference to drawings showing the multiple exemplary embodiments. Additional features and advantages essential to the invention may be found in the drawings and their description.

Figure 2:
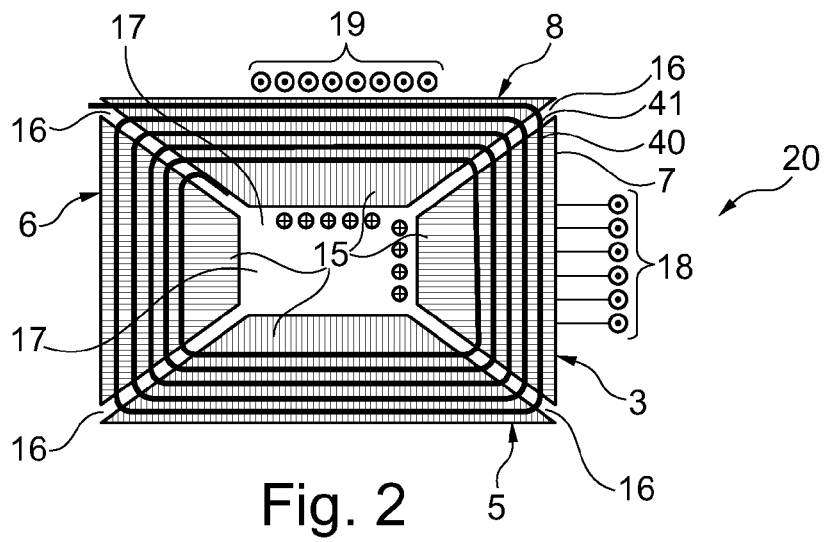
Figure 3:
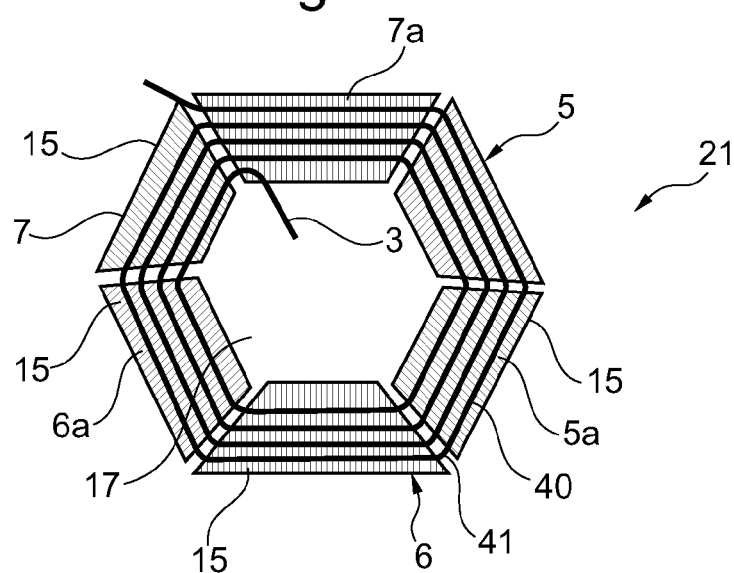
Figure 4:
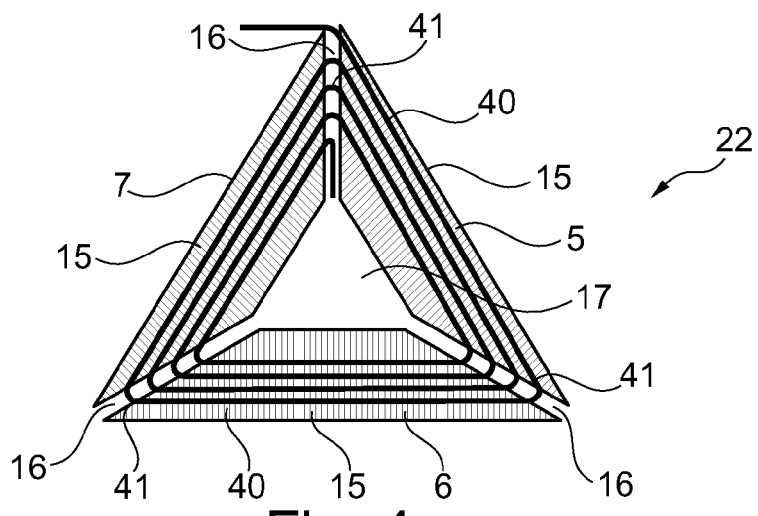
Figure 5:
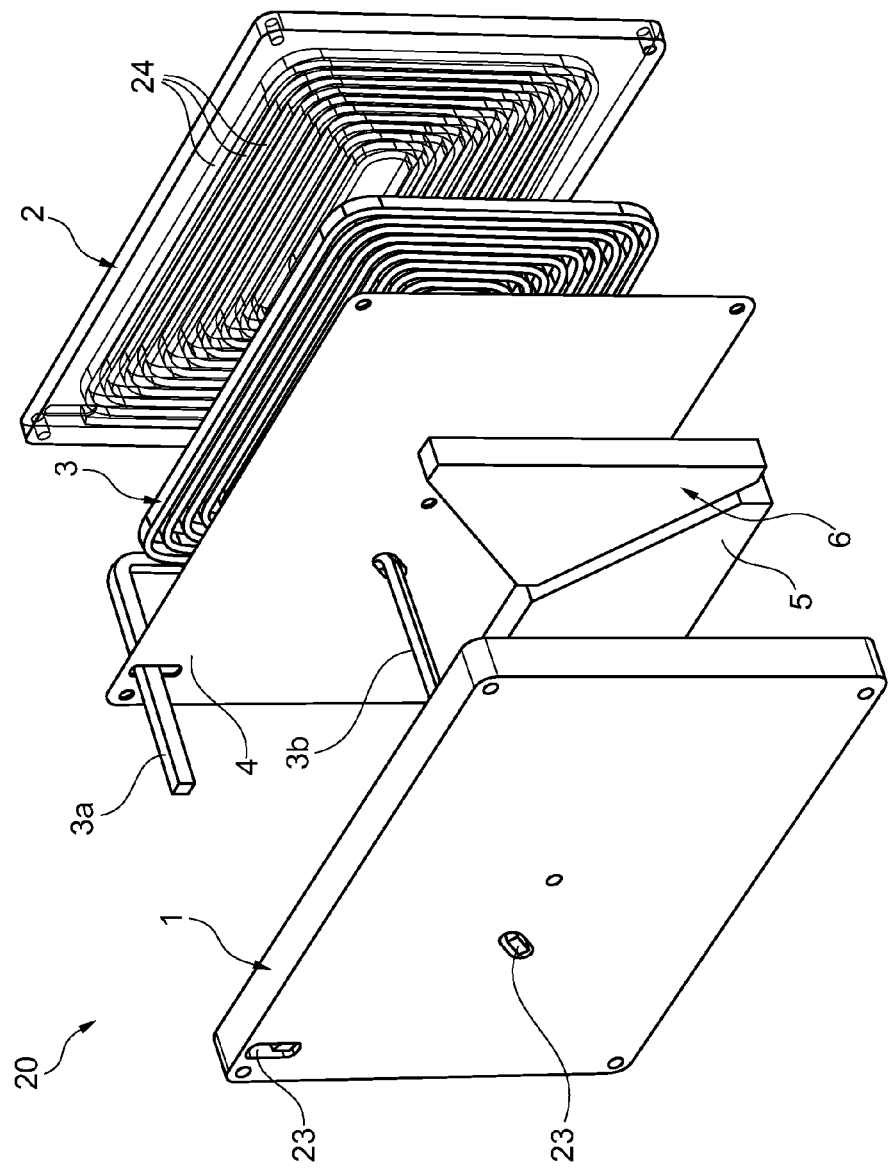
Figure 6:
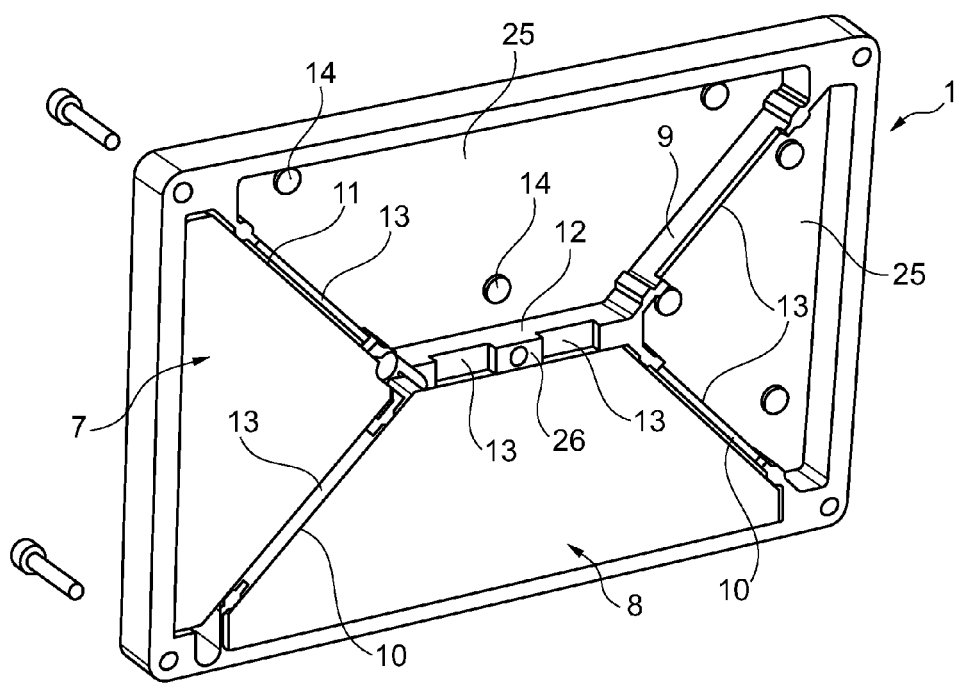
Figure 7:
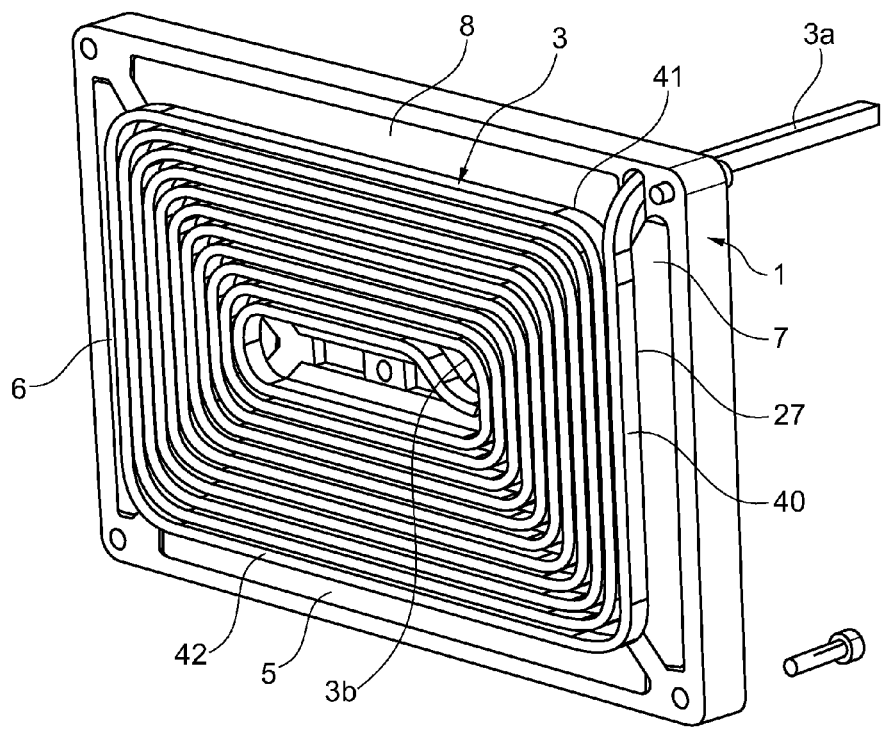
Figures 7A, 7B:
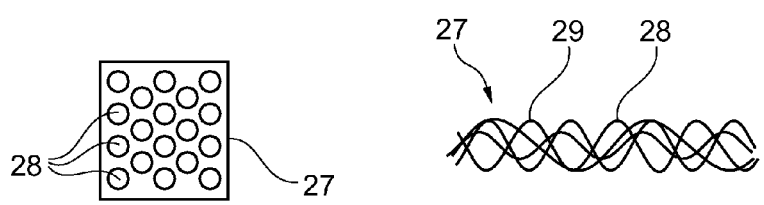
Figure 8:
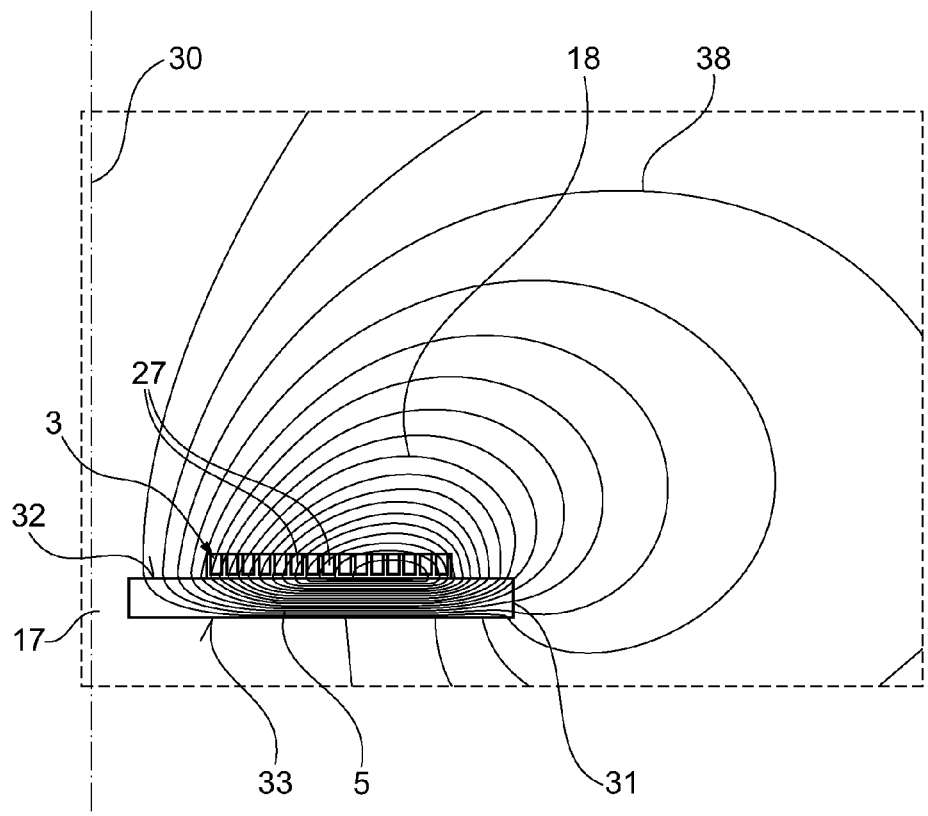
Figure 9:
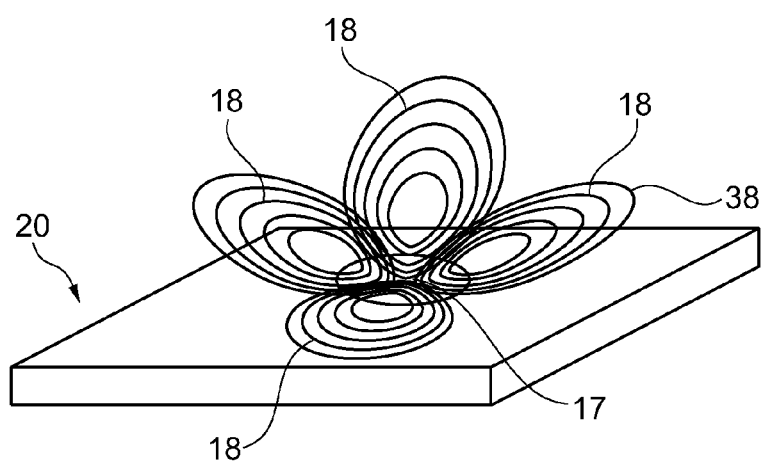
Figure 10:
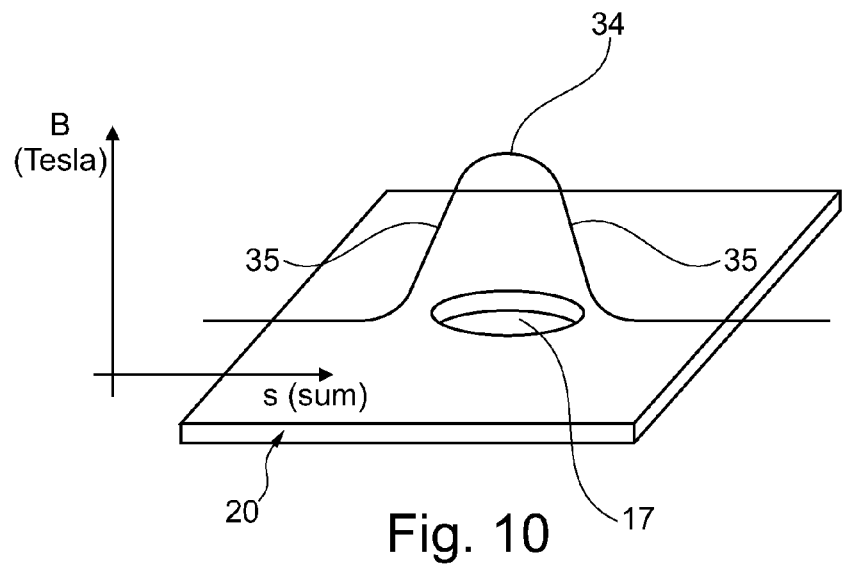
Figure 11:
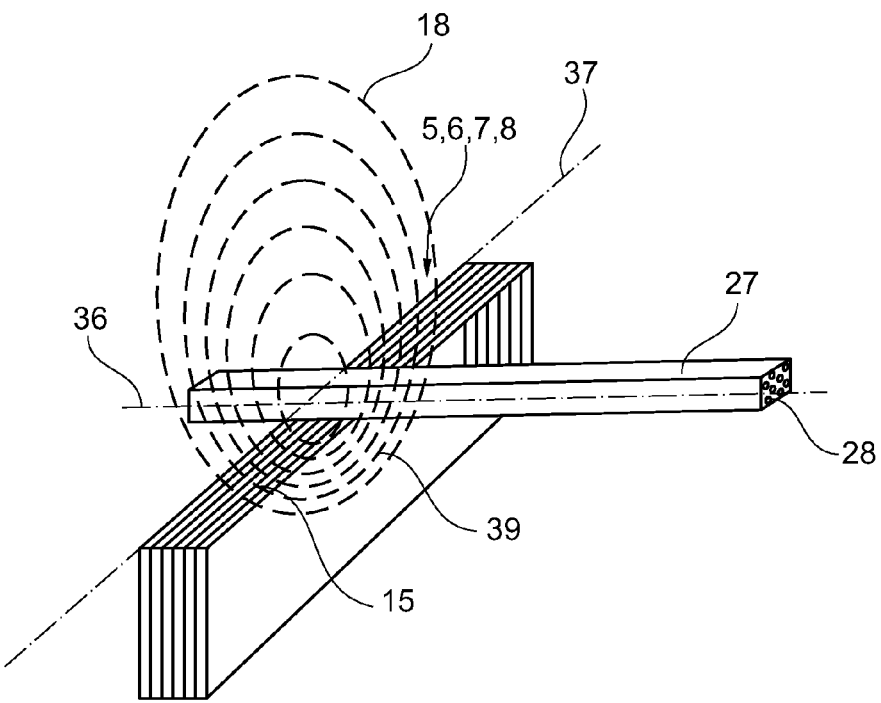

Shown are:

FIG. 1 a perspective exploded view of a first embodiment of a magnetic field applicator in the form of a rectangular coil, FIG. 2 a perspective top view of the arrangement according to FIG. 1, FIG. 3 a top view of a modified first embodiment, FIG. 4 a top view of a modified second embodiment, FIG. 5 a depiction of the rectangular coil rotated 90° as compared to FIG. 1, FIG. 6 a perspective depiction of a top view of the core carrier, FIG. 7 a perspective view of the coil with the coil carrier, FIG. 7A a cross section of a rectangular conductor, FIG. 7B a schematic view of the path of the round strand in the rectangular conductor, FIG. 8 the field line paths of the coil with a sector iron core on one side of the rectangular coil, FIG. 9 a schematic and highly simplified view of the rectangular distribution of the magnetic field resulting from the magnetic field path according to FIG. 8, FIG. 10 a comparison of the magnetic field strengths along the path relative to the surface of the rectangular coil, FIG. 11 a schematic view of the path of the rectangular conductor relative to the layered iron sheet and depiction of the magnetic field resulting therefrom.

FIG. 1 shows a schematic depiction of the structure of a magnetic field applicator designed as a rectangular coil. It essentially comprises a lower core carrier 1 having an approximate shell shape and preferably made of a plastic material. The plastic material forms a shell that is open in the upward direction and in the interior of which a number of bars 9, 10, 11 running inward in an approximate star shape are disposed. The shell is shown again in FIG. 6 in an enlarged depiction. The depiction in FIG. 6 and its description are hereby incorporated by reference.

A total of four receiving spaces 25 is formed in the shell that are formed by the bars 9, 10, 11 running radially inward, with the bars 9, 10, 11 meeting in the central region in the vicinity of a spacer 12 on which a guide part 26 is disposed in a raised fashion. The guide part 26 serves to screw the upper cover plate formed by the coil carrier 2 onto the top of the core carrier 1.

Supporting elements 14 are disposed in the receiving spaces 25 of the core carrier 1 on the base side, with a total of four sector iron cores 5, 6, 7, 8 being placed upon said supporting elements such that the receiving space 25 is filled by the inserted sector iron core.

In the depictions according to FIG. 1 and FIG. 6, two receiving spaces 25 are filled with associated sector iron cores 7, 8 or the sector iron cores 7, 8 have already been placed there.

The bars 9-12 comprise upward-directed recesses 13 that are suitable for filling with a thermosetting coercive material. This material may be, for example, a thermosetting plastic material enriched, for example, with cobalt shavings in order to also produce a magnetically conductive surface on the faces of the sector iron cores 5-8 so as to allow the most complete conducting level possible below the coil carrier and the coil 3.

* * *

It is preferable for the highly coercive casting material to be an elastomer that is able to absorb and dampen any vibrations of the sector iron cores 5-8.

It is important for each sector iron core 5-8 to be comprised of a plurality of iron sheets 15 that are stacked and insulated from one another and that are embodied, for example, as transformer sheets.

Therefore, in order to create such a sector iron core 5-8, an approximately square or rectangular basic form is produced in which a plurality of iron sheets 15 placed upright is disposed. These iron sheets are adhered to one another, for example. Using a suitable laser cutting method, the required contours of the individual sector iron cores 5-8 are cut out so as to obtain the shape according to FIGS. 2 to 4.

Instead of the laser cutting method, the iron sheet packet may be sawed in a mechanical fashion and the sawed faces may be ground in order to prevent the iron sheets from touching one another in their sawed face region.

The iron sheets 15 are therefore electrically insulated from one another and, for example, designed as transformer plates.

It is important for the layering of the iron sheets 15 to be designed in such a way that they are located upright and perpendicular to the coil plane of the coil 3. This will be described in greater detail with reference to FIG. 11.

The sector iron cores 5-8 that are placed in the receiving spaces 25 of the core carrier 1 are covered above by an insulation plate 4 made of an electrically insulating plastic.

The insulation plate 4 serves as a cover plate for the coil 3 disposed thereabove, which is accommodated in a coil carrier 2.

Additional details will be provided with reference to FIGS. 6 and 7.

FIG. 2 shows a schematic top view of a rectangular coil 20 according to FIG. 1. It may be seen that the layering direction of the iron sheets 15 is always located perpendicular to the circumferential edges of the sector iron cores 5, 8 and that the field line bundle 18 resulting therefrom is always directed outward, for example, upward, such that the field line bundle 18 runs on the same plane as the plane of the iron sheets 15. This is shown in greater detail in FIG. 8 and FIG. 11.

Therefore, in the exemplary embodiment according to FIGS. 2 to 4, it is important for all of the coil wires of the coil 3 to run in a straight line to the greatest extent possible, i.e., for the bend radii located therebetween to be minimized, and for said wires to be disposed parallel to one another and to lie in the same plane. The invention is not limited to the arrangement of the coil conductor wires in the coil 3 in a single plane. Likewise, in a different embodiment, it is possible for multiple planes of coil conductor wires to overlap. Instead of a single coil, therefore, it is also possible for multilayer coils to be present.

FIG. 3 shows a polygonal coil 21 instead of a rectangular coil 20 according to FIG. 2, with the same reference characters being used for the same parts. Here, it may be seen that differently shaped sector iron cores 5, 5a, 6, 6a, and 7, 7a are present; said sector iron cores should rest against one another on the edges to the greatest extent possible and the gap 16 resulting therefrom should be minimized to the greatest extent possible.

For reasons of better clarity alone, the layer directions of the iron sheets 15 are shown in an exaggerated fashion, just as the width of the gap 16 is shown in an exaggerated fashion.

Likewise, the figures show that a central recess is formed in the interior of the coil 3. The central recess 17 is formed by the inner circumference of the sector iron cores 5-8 adjacent to one another. However, the invention is not limited to this. The sector iron cores 5 may also extend completely into the inner space such that the central recess 17 approaches zero or disappears entirely.

Furthermore, FIG. 4 shows another arrangement of sector iron cores 5, 6, 7 that combine to form a triangular coil 22.

In addition to these basic shapes according to FIGS. 2 to 4, all combinations of the arrangements of the coils 20-22 shown in FIGS. 2 to 4 may be provided. In all embodiments, it is important for the layer orientation of the layered iron cores 15 in the individual sector cores 5-8 to be perpendicular to the longitudinal extension of the conductor wires of the coil 3, as will be shown below with reference to FIG. 11.

With this technical teaching, an extraordinarily high upward-directed field line concentration is achieved for the first time in which an approximately spherical field is obtained that extends above the central recess 17 and generates only a small amount of heat with a small amount of eddy current losses. This result has not been possible up to now.

FIG. 5 shows a depiction of a rectangular coil 20 according to FIG. 1 rotated by 90°, with the interior view of the coil carrier 2 being discernible. The coil carrier is preferably made of a plastic material into which the guide tracks 24 have been ground in which the individual spiral-wound rectangular conductors 27 of the coil 3 are placed and insulated from one another.

The coil 3 placed in the guide tracks 24 of the coil carrier 2 can also be poured in.

The coil ends 3a, 3b are guided through recesses in the insulation plate 4, extend through recesses 23 in the core carrier 1, and are connected to a direct current source that is subject to a pulse contact control.

FIG. 6 shows additional details of the structure of the core carrier, which have already been discussed in conjunction with FIG. 1.

While the layer direction of the iron sheets 15 was only partially and schematically filled in in FIG. 1 for the sake of a simpler drawing, FIG. 6 omits the depiction of the layer direction of iron sheets 15.

In a schematic depiction, FIG. 2 shows that, above each sector iron core 5, 6, 7, 8, its own field line bundle 18, 19 is generated and that the field line bundle generated relative to the sector iron cores 5 and 6 was omitted for the sake of improved clarity. Overall, this results in a spherical, upward-directed magnetic field, which will be described below.

Thus, an extensively homogenous magnetic field is generated above the base surface of the magnetic field applicator that is preferably directed upward and that, in its base form, approximately corresponds to the rectangular shape of the applicator. Because, in a preferred embodiment, the applicator is designed as a rectangular coil 20 having a rectangular core carrier 1, the resulting shape is not precisely spherical but rather ovoid.

The coil conductors, for example, the rectangular conductors 27 of the coil 3, should form an extensively straight stretch 40 in comparison to the short bend radii 41. The exemplary embodiments according to FIGS. 2 and 4 approximate this desired ideal. The ratio of the length of the coil conductors laid in a straight line to the length of the coil conductors laid in the bend radius 41 is a ratio of 10:1 up to 50:1. The ratio numbers given here should be considered only examples of length ratios; they do not limit the scope of the invention because they are to be understood only as examples.

FIG. 7 shows the core carrier 1 with the laid sector iron cores 5-8 upon which the coil 3 is placed.

FIG. 7A shows a section of a rectangular conductor 27 of the coil 3. It may be seen that the rectangular volume is filled by a plurality of round strands 28 that are insulated from one another and in that form the longitudinal axis of the rectangular conductor 27 in such a twisted state according to FIG. 7B, such that each round strand runs once along the outer surface of the rectangular conductor and once in the interior space thereof. In this manner, instances of magnetic displacement are prevented.

FIG. 8 shows a schematic view of a field line path of the field line 38 over the upright conductors 27, which form the coil 3, with the same arrangement of sector iron cores being disposed on the opposite side of the recess 17 and symmetrically to the symmetrical axis 30.

Here, it may be seen that a maximum effective field line concentration results on the upper flat side of the sector iron core 5 that also enters on the face side 31 of the sector iron core 5. Only a few field lines are projected downward, resulting in the effectiveness of the sector iron core 5 comprised of layered iron sheets 15.

A high concentration of the field lines is present in the inner space of the sector iron core 5 and only a low magnetic field density is projected downward on the flat side 33.

FIG. 9 shows a schematic and highly simplified view of the desired spherical field that extends over the central recess 17 of the rectangular coil 20 and that extends with the maximum possible field line concentration upward into the abdomen of a human body sitting thereon, preferably into the urogenital tract, and fills this region of the body as homogenously and continuously as possible.

FIG. 10 shows a comparison of the field line strengths (ordinates) over the surface of the rectangular coil 20. It may be seen that the maximum of the field line strengths results above the central recess 17 and that, adjacent to the central region, a decrease 35 decreasing to all sides can be observed. In reality, the field line distribution is three-dimensional and is shown in a simplified fashion for graphic reasons only. The distribution is therefore axially symmetrical and present above the central recess 17.

FIG. 11 shows the principle of the invention. The longitudinal extension 36 of the rectangular conductors 27 extends perpendicular to the plane 39 of the layered iron sheets 15. The iron sheets 15 also form a longitudinal extension 37 that is oriented perpendicular to the longitudinal extension 36 of the rectangular conductors 27. Therefore, a field line bundle 18 results around the longitudinal extension 36 of the rectangular conductor 27, with the field line density being dense in the layered iron sheet 15 and being guided through the iron sheet with a small amount of losses.

Therefore, the plane of the field line bundle 18 is located in the same plane 39 as the layered iron sheets 15. In this manner, only a small amount of eddy currents are generated in the iron sheets 15 and only very minor heat generation results therefrom. For this reason, the magnetic field applicator does not require any cooling, even if very high currents (>1000 A) with short pulses (<1 ms) are applied repetitively up to 250 Hz.

KEY TO DRAWINGS

1 Core carrier
2 Coil carrier
3 Coil
3a Coil end
3b Coil end
4 Insulation plate
5 Sector iron core
6 Sector iron core
7 Sector iron core
8 Sector iron core
9 Bar
10 Bar
11 Bar
12 Spacer
13 Recess
14 Supporting element
15 Iron sheet (layered)
16 Gap
17 Central recess
18 Field line bundle
19 Field line bundle
20 Rectangular coil
21 Polygonal coil
22 Triangular coil
23 Recess
24 Guide track
25 Receiving space
26 Guide part
27 Rectangular conductor
28 Round strand (insulated)
29 Twisting
30 Symmetrical axis
31 Face side
32 Flat side, upper
33 Flat side, lower
34 Maximum
35 Decrease
36 Longitudinal extension (of 27)
37 Longitudinal extension (of 15)
38 Field line
39 Planes (of 5-8)
40 Straight stretch
41 Bend radius

The invention claimed is:

1. A magnetic field applicator for magnetic stimulation of body tissues comprising a core carrier (1) in which a plurality of magnetically conductive flow guide pieces comprised of layered iron sheets is disposed, upon which at least one live coil (3) is disposed that generates an upward-emitted magnetic field having a plurality of field line bundles (18), wherein the magnetic field applicator comprises a polygonal coil (3) that is wound as a pancake coil in one or more planes in such a way that direction of individual coil conductors (27) is selected such that the coil conductors (27) run in pieces in a predominantly straight line and perpendicular to a plane of the flow guide pieces that are made of layered sector iron cores (5-8), wherein the sector iron cores (5-8) are poured into the core carrier (1) with a magnetically conductive, electrically insulating, vibration-absorbing, hardening plastic material.

2. The magnetic field applicator according to claim 1, wherein the sector iron cores (5-8) disposed evenly on a circumference of the core carrier (1), said sector iron cores forming a virtually closed iron body on whose top and/or bottom side the coil conductors (27) of the coil (3) are disposed.

3. The magnetic field applicator according to claim 2, wherein the coil (3) is embodied as a rectangular or triangular coil.

4. The magnetic field applicator according to claim 3, wherein the coil conductors have a rectangular shape with a cross-section defined by a plurality of conductive wires that are twisted and insulated from one another.

5. The magnetic field applicator according to claim 4, wherein the coil conductors are oriented upright relative to a plane of the sector iron cores (5-8).

6. The magnetic field applicator according to claim 5, wherein the upwardly emitted magnetic field has an approximately spherical shape.

7. The magnetic field applicator according to claim 6, wherein the core carrier (1) comprises a shell opening upward made of a magnetically and electrically nonconductive material and the sector iron cores (5-8) are placed in receiving spaces (25) separated by bars (9-12) in the core carrier.

8. The magnetic field applicator according to claim 1, wherein each sector iron core (5-8) comprises a plurality of iron sheets (15), and a layering direction of the plurality of iron sheets (15) lies perpendicular to circumferential edges of the sector iron cores (5-8).

9. The magnetic field applicator according to claim 1, wherein a ratio of a length (40) of the coil conductors (27) laid in a straight line to a length of the coil conductors (27) laid in a bend radius (41) is a ratio of 10:1 up to 50:1.

10. A magnetic field applicator for magnetic stimulation of body tissues comprising:
a core carrier (1);
a plurality of magnetically conductive electrically insulating flow guide pieces comprised of layered iron sheets forming layered sector iron cores (5-8) and disposed on the core carrier (1);
at least one live coil (3) disposed on the plurality of magnetically conductive flow guide pieces that generates an upward-emitted magnetic field having a plurality of field line bundles (18), wherein the at least one live coil (3) comprises a polygonal coil (3) that is wound as a pancake coil in one or more planes, the polygonal coil (3) comprising individual coil conductors disposed in a in a predominantly straight line and perpendicular to a plane of the plurality of magnetically conductive flow guide pieces, and
wherein the sector iron cores (5-8) are poured into the core carrier (1) with a magnetically conductive, electrically insulating, vibration-absorbing, material.

11. The magnetic field applicator according to claim 10, wherein the sector iron cores (5-8) disposed evenly on a circumference of the core carrier (1), said sector iron cores forming a virtually closed iron body on whose top and/or bottom side the coil conductors (27) of the coil (3) are disposed.

12. The magnetic field applicator according to claim 10, wherein the coil (3) is embodied as a rectangular or triangular coil.

13. The magnetic field applicator according to claim 10, wherein the coil conductors have a rectangular shape with a cross-section defined by a plurality of conductive wires that are twisted and insulated from one another.

14. The magnetic field applicator according to claim 10, wherein the coil conductors are oriented upright relative to a plane of the sector iron cores (5-8).

15. The magnetic field applicator according to claim 10, wherein the upwardly emitted magnetic field has an approximately spherical shape.

16. The magnetic field applicator according to claim 10, wherein the core carrier (1) comprises a shell opening upward made of a magnetically and electrically nonconductive material and the sector iron cores (5-8) are placed in receiving spaces (25) separated by bars (9-12) in the core carrier.

17. The magnetic field applicator according to claim 10, wherein each sector iron core (5-8) comprises a plurality of iron sheets (15), and a layering direction of the iron sheets (15) lies perpendicular to circumferential edges of the sector iron cores (5-8).

18. The magnetic field applicator according to claim 10, wherein a ratio of a length (40) of the coil conductors (27) laid in a straight line to a length of the coil conductors (27) laid in a bend radius (41) is a ratio of 10:1 up to 50:1.

\* \* \* \* \*